US005981826A

United States Patent [19]
Ku et al.

[11] Patent Number: 5,981,826
[45] Date of Patent: Nov. 9, 1999

[54] POLY(VINYL ALCOHOL) CRYOGEL

[75] Inventors: David N. Ku, Atlanta; Linda G. Braddon, Alpharetta; David M. Wootton, Atlanta, all of Ga.

[73] Assignee: Georgia Tech Research Corporation, Atlanta, Ga.

[21] Appl. No.: 08/932,029

[22] Filed: Sep. 17, 1997

Related U.S. Application Data

[60] Provisional application No. 60/045,875, May 5, 1997.

[51] Int. Cl.$^6$ ............................... A61F 2/02; A61F 13/00
[52] U.S. Cl. ................................ 623/11; 623/901; 602/49
[58] Field of Search .................................... 623/1, 11, 12, 623/13, 15; 602/41, 48, 49

[56] References Cited

U.S. PATENT DOCUMENTS

| | | | |
|---|---|---|---|
| 4,734,097 | 3/1988 | Tanabe et al. | 623/11 |
| 5,288,503 | 2/1994 | Wood et al. | 424/497 |
| 5,343,877 | 9/1994 | Park | 623/16 |
| 5,512,475 | 4/1996 | Naughton et al. | 623/15 |

OTHER PUBLICATIONS

Study of cryostructurization of polymer systems, Colloid & Polymer Science, v. 264, pp. 19–24 (1986); V.I. Lozinsky, E.S. Vainerman, L. V. Domotenko, A.M. Mamtsis, E.F. Titova, E.M. Belavtseva, and S.V. Rogozhin.

Thermal and rheological properties of poly (vinyl alcohol) hydrogels prepared by repeat cycles of freezing and thawing, Makromol. Chem., v. 189, pp. 871–880 (1988); Mimeo Watase, Katsuyoshi Nishinari.

Polyvinyl Alcohol Cryogel: An Ideal Phantom Material for MR Studies of Arterial Flow and Elasticity, Magnetic Resonance in Medicine, v. 37, pp. 314–319 (1997); Kenneth C. Chu, Brian K. Rutt.

Poly (vinyl alcohol) hydrogels prepared by freezing—thawing cyclic processing, Polymer, v. 33, pp. 3932–3936 (1992); Shauna R. Stauffer and Nikolaos A. Peppas.

*Primary Examiner*—David J. Isabella
*Assistant Examiner*—John M. Black
*Attorney, Agent, or Firm*—Lyon & Lyon LLP

[57] ABSTRACT

The present invention includes a poly(vinyl alcohol) hydrogel construct having a wide range of mechanical strengths for use as a human tissue replacement. A process in connection with the present invention eliminates any step involved with dehydration of the hydrogel prior to implantation thereof. The hydrogel construct may include a tissue scaffolding, a load bearing surface within a joint, or any other structure which is suitable for supporting the growth of tissue.

30 Claims, No Drawings

POLY(VINYL ALCOHOL) CRYOGEL

RELATED APPLICATIONS

This application claims priority to provisional application Ser. No. 60/045,875, filed on May 5, 1997, which is incorporated herein by reference in its entirety.

FIELD OF THE INVENTION

The present invention relates generally to hydrogel biomaterials for use as tissue replacements or scaffolds. More specifically, the present invention relates to a poly(vinyl alcohol) ("PVA") cryogel for use as a structural member or as a tissue scaffolding in vivo.

DESCRIPTION OF THE PRIOR ART

Most tissues of the living body include a large weight percentage of water. Therefore, in a selection of a prosthesis, a hydrous polymer (hydrogel) is considered to be superior in biocompatibility as compared to nonhydrous polymers. Although hydrogels do less damage to tissues than nonhydrous polymers, conventional hydrogels have historically included a serious defect in that they are inferior in mechanical strength. For that reason, the use of hydrogels has been extremely limited in the past.

Artisans have proposed a number of hardening means for improving mechanical strength. Some hardening means include treating the hydrogel with a cross-linking agent such as formaldehyde, ethylaldehyde, glutaraldehyde, terephthalaldehyde or hexamethylenediamine. Unfortunately, however, it is well known that those treatments decrease the biocompatibility of the hydrogel biomaterial. One example of a popular hydrogel which has been proposed for use as a biomaterial is PVA.

Numerous references generally describe the process of freezing and thawing PVA to create a hydrogel: Chu et al., Poly(vinyl alcohol) Cryogel: An Ideal Phantom Material for MR Studies of Arterial Elasticity, Magnetic Resonance in Medicine, v. 37, pp. 314–319 (1997); Stauffer et al., Poly (vinyl alcohol) hydrogels prepared by freezing-thawing cyclic processing, Polymer, v.33, pp. 3932–3936 (1992); Lozinsky et al., Study of Cryostructurization of polymer systems, Colloid & Polymer Science, v. 264, pp. 19–24 (1986); Watase, Thermal and rheological properties of poly (vinyl alcohol) hydrogels prepared by repeated cycles of freezing and thawing, Makromol. Chem., v. 189, pp. 871–880 (1988). The disclosure from these references is hereby incorporated by reference.

Another such reference is U.S. Pat. No. 4,734,097, issued to Tanabe, et al. on Mar. 29, 1988 ("Tanabe"). Tanabe proposes the construct of a molded hydrogel obtained by pouring an aqueous solution containing not less than 6% by weight of a polyvinyl alcohol which has a degree of hydrolysis not less than 97 mole percent and an average polymerization degree of not less than 1,100 into a desired shape of a vessel or mold, freeze molding an aqueous solution in a temperature lower than minus 5° C., then partially dehydrating the resulting molded product without thawing it up to a percentage of dehydration not less than 5 weight percent, and if required, immersing the partially hydrated molded part into water to attain a water content thereof in the range of 45 to 95 weight percent.

The disadvantage to Tanabe, et al. is that it necessarily requires a step of dehydration in preparing the PVA hydrogel. There are several disadvantages associated with the dehydration step. First, the dehydration step adds additional time and capital expense associated with machinery which must accomplish the dehydration step. Additionally, dehydration may denature bioagents included in the hydrogel.

With the foregoing disadvantages of the prior art in mind, it is an object of the present invention to provide a biocompatible PVA hydrogel which includes a mechanical strength range sufficient for a wide variety of applications as biomaterial.

It is another object of the present invention to provide a method for producing the PVA hydrogel which precisely controls the mechanical strength thereof, and which eliminates any dehydration step prior to implantation.

Other objects, features and advantages of the present invention will become apparent upon reading the following specification.

SUMMARY OF THE INVENTION

Generally speaking, the present invention relates to a novel poly(vinyl alcohol) ("PVA") cryogel tissue replacement construct and a process for making the construct.

More specifically, the present invention relates to a non-dehydrated PVA cryogel construct which is capable of being molded into a number of shapes, and which is capable of retaining a wide range of mechanical strengths for various applications. The PVA cryogel may comprise a PVA polymer starting material in the form a dry powder wherein the degree polymerization of the PVA may range approximately 500 to 3,500. The tissue replacement in accordance with the present invention may include approximately 2 to approximately 40 parts by weight PVA and approximately 98 to 60 parts by weight water. Additionally, the hydrogel may include an isotonic saline solution substitute for water to prevent osmotic imbalances between the tissue replacement and surrounding tissues. The replacement may also include a number of bioactive agents including, but not limited to, heparin, growth factors, collagen cross-linking inhibitors such as $\beta$-aminopropeonitrile ($\beta$APN), matrix inhibitors, antibodies, cytokines, integrins, thrombins, thrombin inhibitors, proteases, anticoagulants and glycosaminoglycans.

A process in accordance with the present invention involves mixing water with the PVA crystal to obtain a non-dehydrated PVA hydrogel, thereby eliminating the dehydration step prior to implantation. More specifically, the present invention involves freezing and thawing the PVA/water mixture to create an interlocking mesh between PVA polymer molecules to create the PVA cryogel. The freezing and thawing step may be performed at least twice, with mechanical strength of the PVA cryogel increasing each time the freezing and thawing step is performed. The process may include the further steps of pouring the PVA/water mixture into a mold, freezing the mixture, and the thawing the mixture to obtain a non-dehydrated construct. Additionally, the process may also include the step of removing the construct from the mold, immersing the construct in water, freezing the construct while immersed in water and thawing the construct while immersed in water to increase the mechanical strength of the construct. The process may also include the steps of adding bioactive agents to the hydrogel.

Because it can be manufactured to be mechanically strong, or to possess various levels of strength among other physical properties, it can be adapted for use in many applications. The cryogel also has a high water content which provides desirable properties in numerous applications. For example, the cryogel tissue replacement construct is especially useful in surgical and other medical applications as an artificial material for replacing and reconstructing soft tissues in humans and other mammals. Soft tissue body parts which can be replaced or reconstructed by the cryogel include, but are not limited to, vascular grafts, heart valves, esophageal tissue, skin, corneal tissue, cartilage, meniscus, and tendon. Furthermore, the cryogel may also serve as a cartilage replacement for anatomical structures including, but not limited to an ear or nose. The inventive cryogel may also serve as a tissue expander. Additionally, the inventive cryogel may be suitable for an implantable drug delivery device. In that application, the rate of drug delivery to tissue will depend upon cryogel pore size and degree of intermolecular meshing resulting from the freeze/thaw device. The rate of drug delivery increases with the number of pores and decreases with an increasing degree of intermolecular meshing from an increased number of freeze/thaw cycles.

The cryogel is especially suitable for vascular grafts and heart valve replacements, because the cryogel is thromboresistant, and because of the particular mechanical and physiological requirements of vascular grafts when implanted into the body. The cryogel may also be used for contact lenses, as a covering for wounds such as burns and abrasions, and in other applications wherein a mechanically strong material is preferred.

Other objects, features and advantages of the present invention will become apparent upon reading the following specification, when taken in conjunction with the accompanying examples.

Reference will now be made in detail to the description of the invention. While the invention will be described in connection with specific examples, there is no intent to limit it to the embodiment or embodiments disclosed therein. On the contrary, the intent is to cover all alternatives, modifications and equivalents included within the spirit and scope of the invention as defined by the appended claims.

DETAILED DESCRIPTION OF THE PREFERRED EMBODIMENTS

In a preferred embodiment, a process in accordance with the present invention produces the cryogel in a two stage process. In the first stage a mixture of poly(vinyl alcohol) and water is placed in a mold, and repeatedly frozen and thawed, in cycles, until a suitable cryogel is obtained. In a second stage, the cryogel is removed from the mold, placed in water, and undergoes at least one other freeze-thaw cycle until desirable mechanical properties are achieved. In the first stage, a series of sequential steps is employed comprising: (i) mixing water with poly(vinyl alcohol) to obtain a poly(vinyl alcohol)/water mixture; (ii) freezing the mixture; (iii) thawing the mixture; and (iv) repeating the freeze and thaw steps, as necessary, until a poly(vinyl alcohol) cryogel having the desired physical properties is obtained. If necessary, the second stage may then be employed.

Poly(vinyl alcohol) useful for the invention is typically obtained as a dry powder or crystal, and can vary based upon several factors, including morlecular weight, degree of polymerization, and degree of saponification (or hydrolysis). The molecular weight of the poly(vinyl alcohol) can vary, and can be chosen depending upon the particular application envisioned for the cryogel. Generally, increasing the molecular weight of the poly(vinyl alcohol) increases the tensile strength and tensile stiffness, and thereby improves the properties of constructs such as vascular grafts, wherein increased strength is desirable. In other applications, such as cartilage, lower molecular weight poly(vinyl alcohol) can be employed because lower tensile strength and lower tensile stiffness are desirable. Poly(vinyl alcohol) having an average molecular weight of from about 11,000 to 500,000 is preferred for practicing the invention. Poly(vinyl alcohol) having an average molecular weight of from about 85,000 to 186,000 is even more preferred for practicing the invention, especially when producing vascular grafts, and poly(vinyl alcohol) having an average molecular weight of from about 124,000 to 186,000 is especially preferred.

The average degree of polymerization for preferred poly(vinyl alcohol)s generally ranges from about 500 to 3500, and poly(vinyl alcohol) having a degree of polymerization of from about 2700 to 3500 is especially preferred. Preferred poly(vinyl alcohol) typically has a degree of saponification (or hydrolysis) in excess of 80%, more preferred poly(vinyl alcohol) is saponified (or hydrolyzed) in excess of about 97%, and even more preferred poly(vinyl alcohol) is saponified (or hydrolyzed) in excess of 99%. High molecular weight poly(vinyl alcohol) in crystal form, available from the Aldrich Chemical Company, is a good example of a poly(vinyl alcohol) suitable for practicing the present invention.

The water that is mixed with the poly(vinyl alcohol) is preferably deionized and ultra filtered to minimize the potential for any contamination of the poly(vinyl alcohol). The mixture is preferably prepared by mixing from about 2 to about 40 parts by weight poly(vinyl alcohol) with about 98 to 60 parts by weight water. The concentration of the poly(vinyl alcohol) contributes to the stiffness of the cryogel, and can thus be chosen depending upon the stiffness of the material one desires to obtain. A more preferable mixture is obtained by mixing from about 10 to about 20 parts poly(vinyl alcohol) with from about 80 to about 90 parts by weight water, and an especially preferred mixture is obtained by mixing about 15 parts poly(vinyl alcohol) with about 85 parts by weight water. Isotonic saline (0.9% by weight NaCl, 99.1% water) or an isotonic buffered saline may be substituted for water to prevent osmotic imbalances between the material and surrounding tissues if the cryogel is to be used as a soft tissue replacement.

After the poly(vinyl alcohol) and water are mixed, it is often necessary to process the mixture to ensure that the poly(vinyl alcohol) is adequately solubilized. Suitable solubilization processes are generally known in the art and include, for example, heating the mixture, altering the pH of the mixture, adding a solvent to the mixture, subjecting the mixture to external pressure, or a combination of these processes. A preferred method is to heat the mixture in an autoclave, at a temperature of about 120° C., and a pressure of about 17 p.s.i., for about 25 minutes, is typically effective to solubilize the poly(vinyl alcohol) and, in addition, to sterilize the mixture before further processing.

After the mixture has been prepared, air bubbles that may have become entrapped in the mixture should be removed. The solution can be allowed to sit for a period of time, preferably at an elevated temperature, to allow the air bubbles to rise out of solution. The mixture can also be placed in a sterile vacuum chamber for a short time to bring the bubbles out of solution.

Once prepared, the mixture can be poured into one or more pre-sterilized molds. If needed, the solution in the mold can be allowed to sit upright, or subjected to a vacuum in a vacuum chamber, to remove undesirable air bubbles. The shape and size of the mold may be selected to obtain a cryogel of any desired size and shape. Vascular grafts, for example, can be produced by pouring the poly(vinyl alcohol)/water mixture into an annular mold. The size and dimensions of the mold can be selected based upon the location for the graft in the body, which can be matched to physiological conditions using normal tables incorporating limb girth, activity level, and history of ischemia. Suitable annular molds for producing vascular grafts would include Y-shaped molds, which can be used to produce grafts having vascular branching. The cryogel can also be processed by cutting or otherwise forming the cryogel into the desired form after it has been produced. Although not necessary, molds are preferably capped or sealed to prevent dehydration and to preserve sterility. Typically, the mold is not filled entirely with the solution in order to accommodate for the expansion during freezing that occurs when freezing water.

Molds for practicing the invention can be comprised of many suitable materials that will not react with the poly(vinyl alcohol) solution, that will maintain integrity over the required, temperature range, and that will allow the cryogel to be removed without damaging the cryogel. Suitable materials include but are not limited to natural and synthetic resins, natural and synthetic polymers (including those based upon polycarbonates, acrylates and methacrylates, and poly(vinyl alcohol)), glass, steel, aluminum, brass, and copper, among other materials. Outer molds that are compliant and elastic result in a more complete gelling and better physical properties than molds that are stiff. High pressure in the frozen poly(vinyl alcohol) reduces the stiffness of the resulting gel, and compliant molds reduce the pressure on the poly(vinyl alcohol) while it is frozen. Preferred annular molds are constructed from smooth stainless steel or poly(vinyl chloride) tubes around stainless steel mandrels. More preferred annular molds are constructed of compliant poly(vinyl chloride) or other plastic tubes around stainless steel mandrels.

After the mixture has been poured into the mold, and the mold has been sealed, it is frozen to a temperature preferably below about −5° C., and more preferably below about −20° C. The mixture should preferably be frozen for at least 2 hours, including freezing time, more preferably at least 4 hours, and most preferably from about 4 to about 16 hours. In contrast to methods recited in the prior art, no dehydration step is required, and in a preferred embodiment dehydration is not employed because of the importance of hydration to the final product.

After the mixture has been frozen, the temperature of the mixture is raised and the mixture thawed. It is generally preferable to raise the temperature to from about 5 to about 55° C., and to thaw the solution at such temperature for a period of time of about 2 hours or more, and more preferably at least 4 hours, and most preferably from about 4 to about 16 hours, including thawing time and time at such temperature. It is especially preferable to raise the temperature to about 22° C., and to thaw the mixture at such temperature for about 12 hours. Because the hydrogel is solubilized at higher temperatures, the temperature of the mixture should not generally be raised above about 60° C.

After the mixture has been frozen and thawed once under the foregoing conditions, the process may be repeated, although the exact process conditions need not be repeated for each freeze/thaw cycle. Generally, increasing the number of freeze/thaw cycles increases the tensile strength and tensile stiffness of the cryogel, and can be implemented for applications such as vascular grafts wherein higher strength and stiffness are desired. In other applications, such as cartilage, lower numbers of freeze/thaw cycles can be employed because lower tensile strength and lower tensile stiffness are desirable. It is generally preferred to repeat the freeze/thaw cycle from about 0 to about 15 times, and, in vascular graft applications especially, more preferably from about 2 to about 5 times. Most preferably, the freeze/thaw cycle is repeated twice, for a total of three freeze/thaw cycles in the first stage.

After the material has undergone the first stage of freeze/thaw treatment it is carefully removed from the mold in order to avoid damaging the material, and immediately submerged in a liquid bath, preferably of deionized, sterile water. The material can be removed from the mold in either thawed or frozen state. Moreover, the material can be removed from either part or the entire mold. For example, it may be suitable to retain the mandrels within the material if an annular mold is employed, to prevent the material from deforming. The bath should be large enough so that the material is immersed completely in water, and can be open or closed, but preferably closed to maintain sterility.

The second stage involves further freeze/thaw treatment of the molded material. After the mixture is immersed in water, it is again subjected to one or more freeze/thaw cycles in the second stage of the processing. Again, the conditions for each freeze/thaw cycle in the second stage need not be identical. The mixture should preferably be frozen and thawed from about 1 to about 15 times, more preferably, especially for vascular graft applications, from 1 to 3 times, and most preferably twice, while the mixture is submerged in the water. As in the first stage, increasing the number of freeze/thaw cycles increases the tensile strength and tensile stiffness, and the number of cycles can thus be selected based upon the particular application that is planned for the cryogel.

The conditions under which the freeze/thaw cycles of the second stage are carried out are generally comparable to the conditions observed in carrying out the first stage. After the mixture has undergone the second stage of freeze/thaw cycles, it is ready for use.

The poly(vinyl alcohol) cryogel of the present invention can also comprise a bioactive agent to lend to the cryogel suitable physiological properties for it to be used as a soft tissue replacement. The bioactive agent can be chosen based upon the particular application planned for the replacement, and the particular physiological properties required of the replacement in the application involved. Many such bioactive agents would be released gradually from the cryogel after implantation, and thereby delivered in vivo at a controlled, gradual rate. The cryogel can thus act as a drug delivery vehicle. Other bioactive agents can be incorporated in to the cryogel in order to support cellular growth and proliferation on the surface of the material. Bioactive agents which can be included in the replacement include, for example, growth factors, collagen crosslinking inhibitors such as β-aminopropeonitrile (βAPN) or cis-4-hydroxyproline, matrix inhibitors, antibodies, cytokines, integrins, thrombins, thrombin inhibitors, proteases, anticoagulants, and glycosaminoglycans. Heparins are particularly suitable agents for incorporating into vascular grafts, because of their anticoagulant properties, and thus their ability to inhibit thrombosis on the surface of the cryogel.

In order to embed heparin or other bioactive agents into the cryogel of the present invention any of a pre-sterilized heparin powder, aqueous heparin or aqueous heparin suspension can be mixed into the starting sterile poly(vinyl alcohol)/water mixture. After the heparin or other bioactive agent is incorporated into the poly(vinyl alcohol)/water mixture, it is thermally processed along with the poly(vinyl alcohol)/water mixture according to the process described herein. Heparin and other bioactive agents can also be introduced into the cryogel by placing the cryogel into a bath containing an aqueous solution of the agent and allowing the agent to diffuse into the cryogel.

The concentration of the heparin or other bioactive agent in the mixture may be selected for the particular application involved. For heparin incorporation into a vascular graft, concentrations will typically range from 1 unit/ml. to 1,000,000 units/ml. Lower concentrations will be employed to inhibit coagulation on the graft surface, and higher concentrations will be used where local infusion of heparin into the blood is desired to inhibit thrombosis downstream of the graft, as described in Chen et al., Boundary layer infusion of heparin prevents thrombosis and reduces neointimal hyperplasia in venous polytetrafluoroethylene grafts without systemic anticoagulation, J. Vascular Surgery, v. 22, pp., 237–247 (1995).

The cryogel supports the proliferation of eukaryotic cell cultures. Vascular cells such as endothelial cells, smooth muscle cells, and fibroblasts and other connective tissue cells, can thus be incorporated into the cryogel. Human aortic endothelial cells and human dermal fibroblasts are also compatible with the cryogels of the present invention. Cryogels modified by such cell lines are, in turn, especially well adapted for implantation into the human body, and for use as soft tissue replacement parts in the human body. Indeed, replacement parts modified by such cell lines are better able to adapt and adjust to changing physical and physiological conditions in the body, and thereby to prevent any failure of the cryogel which might otherwise occur. Cryogels modified by such cell lines are, in sum, especially well adapted for implantation in the human body, and for use as replacement parts in the human body. These cellular lines can be incorporated into the cryogel, after it has been produced via standard in-culture protocol generally known in the art. It is especially effective to culture human aortic endothelial cells and human dermal fibroblasts using direct topical seeding and incubation in cell culture medium.

Besides the soft tissue replacement uses set forth for the poly(vinyl alcohol) cryogel, discussed above, the cryogels of the present invention can be used in any application in which poly(vinyl alcohol) cryogels are generally suitable, including as an MR (magnetic resonance) quality control phantom, as an ultrasound or radio frequency thermal therapy transmission pad, as a substitute for an ice bag, as a denture base, and in other medical applications.

Although the following examples set out specific parameters for constructing a PVA hydrogel in accordance with the present invention, the ordinarily skilled artisan will understand that mechanical properties of the PVA hydrogel may be affected by one of four factors. Those factors include: (1) weight percentage of the respective constituents within the hydrogel (e.g. PVA polymer and water); (2) the molecular weight of the PVA starting material; (3) the number of freeze/thaw cycles; and (4) the duration of a freeze cycle. It is also important to note that the freeze/thaw cycle promotes an interlocking mesh or entanglement between molecules of PVA to create the mechanical strength. This is different than the traditional cross link accomplished by the above-referenced cross linking agents which inevitably introduces a toxic agent into the biomaterial, thus decreasing biocompatibility of materials which utilize those cross linking agents.

EXAMPLE 1

A 15% by weight poly(vinyl alcohol) solution was prepared by mixing 17.6 grams of poly(vinyl alcohol) polymer (124,000–186,000 Av. MW), 99+% saponification, available for Aldrich Chemical Company, in 100 ml. of deionized, sterile water. The mixture was placed in a loosely capped container, heated and sterilized at 120° C. and 17 p.s.i. in an autoclave for about 25 minutes. The container was then sealed removed from the autoclave and placed under a sterile ventilation hood. The mixture was then stirred to ensure a homogenous solution. The mixture was poured into sterile syringes, being careful not to generate air bubbles. The poly(vinyl alcohol) solution was then injected upwardly into stainless steel annular molds having stainlesssteel mandrels. The outer tube of the annulus had an inner diameter of 8 mm. which surrounded a 5 mm. diameter mandrel. The time that the solution was exposed to air was minimized in order to prevent evaporation of water. The mold was designed to create a poly(vinyl alcohol) cryogel with approximately a 1.5 mm. wall thickness, 10 cm. long, having a 5 mm. inside diameter. The mold was sealed at both ends using O-rings and rubber caps. Air space, equaling about 8% of the volume of the mold was deliberately maintained in order to allow for expansion while the aqueous solution froze.

The tube was then subjected to three (3) cycles of freezing and thawing. In each of the cycle the tube was frozen by placing it upright in a commercial freezer regulated at about −20° C., and allowing it to air cool for about 12 hours. The tube was then thawed by removing the tube from the freezer and setting it upright under ambient conditions. The tube was allowed to thaw for about 12 hours before being returned to the freezer for another cycle.

After the mixture had been frozen and thawed three times, it was removed from the tube (under a sterile vacuum hood) and immersed in a 50 ml, centrifuge vial containing 35 ml. of deionized, sterile water. There was obtained a translucent to clear, gummy, weak material which was substantially unable to maintain its shape outside of water or other liquid. The material was handled carefully with forceps and immersed in water as quickly as possible. The inner diameter of the material was preserved by keeping the mandrel in place. The container was then sealed and placed in a freezer at about −20° C. The mixture was kept in the freezer for about 12 hours, and then removed and allowed to stand at room temperature for about 12 hours. The freezing and thawing process was repeated once thus, considering the three previous cycles within the mold, the mixture was subjected to a total of five (5) cycles of freezing and thawing.

The material obtained was opaque, elastic, and non-sticky, with mechanical properties very similar to a native artery tissue. The material was tested for mechanical strength according to standards of the Association for the Advancement of medical Instrumentation and the American National Standards Institute, published in Cardiovascular implants—Vascular Prosthesis, ANSI/AAMI VP20-1994, section 8.3.3.3 (pressurized burst strength), and section 8.8 (suture retention strength). The material had a burst pressure of about 540 mm Hg. Specifically, a 6-0 suture was placed 2 mm from the edge of the graft and pulled at a rate of 150 mm/min until it pulled through the graft. The average peak pullout load for the material a suture test was about 289 grams, which is greater than the pullout loads reported in the literature for human artery and vein. Finally, the tensile modulus of elasticity of the material was measured to be approximately $4.0 \times 10^5$ Pa

EXAMPLE 2

A 30% by weight poly(vinyl alcohol) solution was prepared by mixing poly(vinyl alcohol) polymer (124,000–186, 000 Av. MW), 99+% saponification, in deionized, sterile water. As with Example 1, the mixture was placed in a loosely capped container, heated, sealed removed from the autoclave, placed under a sterile ventilation hood, stirred to ensure a homogenous solution, poured into sterile syringes, and injected into the molds according to the process of Example 1. In this example, however, the tube was then subjected to ten (10) cycles of freezing and thawing. The freeze/thaw cycles were similar to that of Example 1, except that the sample was allowed to cool for about 24 hours for each freeze/thaw cycle. The tube was then thawed by removing the tube from the freezer and setting it upright under ambient conditions. The tube was allowed to thaw for about 12 hours before being returned to the freezer for another cycle. The resulting PVA biomaterial was stiff and strong with a burst pressure of approximately 1078 mm Hg.

EXAMPLE 3

A 15% by weight poly(vinyl alcohol) solution was prepared by mixing poly(vinyl alcohol) polymer (89,000–98,000 Av. MW), 99+% saponification, in deionized, sterile water in a manner substantially identical with Example 1 except for the following differences. As with Example 1, the mixture was placed in a loosely capped container, heated, sealed removed from the autoclave, placed under a sterile ventilation hood, stirred to ensure a homogenous solution, poured into sterile syringes, and injected into the molds according to the process of Example 1. In this example, however, the tube was then subjected to five (5) cycles of freezing and thawing. The freeze/thaw cycles were similar to that of Example 1, in that each sample was allowed to cool for about 12 hours for each freeze/thaw cycle. The resulting PVA biomaterial was soft with a burst pressure of approximately 98 mm Hg.

As demonstrated by the above-referenced examples, because the PVA cryogel can be manufactured to be mechanically strong, or to possess various levels of strength among other physical properties depending upon the weight percentage of the PVA starting material with respect to other constituents in solution, freeze time, the number of freeze/thaw cycles, and the freeze temperature. As discussed above, the end product cryogel also has a high water content which provides desirable properties in numerous applications and which prevents the denaturing of additives.

The cryogel tissue replacement construct is especially useful in surgical and other medical applications as an artificial material for replacing and reconstructing soft tissues in humans and other mammals. Soft tissue body parts which can be replaced or reconstructed by the cryogel include, but are not limited to, vascular grafts, heart valves, esophageal tissue, skin, corneal tissue, cartilage, meniscus, and tendon. The cryogel may be formed as an implantable articulating surface for a load bearing joint, whereby the articulating surface may be fixed to bone with screws, sutures, or bioglue such as a collagen glue. Furthermore, the cryogel may also serve as a cartilage replacement for anatomical structures including, but not limited to an ear or nose.

The inventive cryogel may also serve as a tissue expander. Additionally, the inventive cryogel may be suitable for an implantable drug delivery device. In that application, the rate of drug delivery to tissue will depend upon cryogel pore size and degree of intermolecular meshing resulting from the freeze/thaw cycles. The rate of drug delivery increases with the number of pores and decreases with an increasing degree of intermolecular meshing from an increased number of freeze/thaw cycles.

The cryogel is especially suitable for vascular grafts and heart valve replacements, because the cryogel is thromboresistant, and because of the particular mechanical and physiological requirements of vascular grafts when implanted into the body. The cryogel may also be used for contact lenses, as a covering for wounds such as burns and abrasions, and in other applications wherein a mechanically strong material is preferred.

Throughout this application, various publications are referenced. The disclosures of these publications in their entireties are hereby incorporated by reference into this application in order to more fully describe the state of the art to which this invention pertains.

The foregoing description has been presented for purposes of illustration and description. It is not intended to be exhaustive or to limit the invention to the precise examples or embodiments disclosed. Obvious modifications or variations are possible in light of the above teachings. The embodiment or embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly and legally entitled.

What is claimed is:

1. A process for preparing a PVA construct comprising the steps of:
    pouring an aqueous PVA polymer mixture into a mold;
    freezing and thawing said PVA polymer mixture within said mold at least once to create an interlocking mesh between PVA polymer molecules to create the PVA cryogel;
    removing, at least partially, said PVA cryogel from said mold;
    immersing said PVA cryogel in an aqueous solution; and
    freezing and thawing said PVA cryogel at least once while immersed in water.

2. The process of claim 1, comprising the further step, before immersing said PVA cryogel in water, of:
    removing, at least partially, said PVA cryogel from said mold.

3. The process of claim 1, wherein said aqueous PVA polymer mixture comprises a PVA polymer starting material having a molecular weight ranging from approximately 11,000 to approximately 500,000.

4. The process of claim 1, wherein said aqueous PVA polymer mixture is biocompatible and comprises a PVA polymer starting material in the form of a dry powder.

5. The process of claim 1, wherein said aqueous PVA polymer mixture comprises a PVA starting material in the form of a dry powder, and further wherein a degree of polymerization of the PVA starting material ranges from approximately 500 to approximately 3500.

6. The process of claim 1, wherein said aqueous PVA polymer mixture comprises a PVA starting material in the form of a dry powder with a degree of hydrolysis in excess of approximately 80 percent.

7. The process of claim 1, wherein said aqueous PVA polymer mixture comprises a PVA starting material in the form of a dry powder with a degree of hydrolysis in excess of approximately 99 percent.

8. The process of claim 1, wherein said aqueous PVA polymer mixture comprises approximately 2 to approximately 40 parts by weight PVA and approximately 98 to approximately 60 parts by weight water.

9. The process of claim 1, wherein said aqueous PVA polymer mixture comprises approximately 20 to approximately 40 parts by weight PVA and approximately 60 to approximately 80 parts by weight water.

10. The process of claim 1, wherein said aqueous PVA polymer mixture comprises an isotonic saline solution to prevent osmotic imbalances between the tissue replacement and surrounding tissues.

11. The process of claim 10, wherein said isotonic saline solution comprises approximately 0.9 percent NaCl and approximately 99.1 percent water.

12. The product according to the process of claim 1.

13. The product of claim 12, further comprising a bioactive agent.

14. The product of claim 13, wherein said bioactive agent is selected from the group consisting of: a heparin, a βAPN, an antibody, a cytokine, an integrin, a protease, a matrix inhibitor, an anticoagulant, a sphyngolipid, a thrombin, a thrombin inhibitor, and a glycosaminoglycan.

15. The product of claim 1 comprising a tissue replacement.

16. The product of claim 1 comprising a tissue scaffold.

17. The product of claim 16 wherein said tissue scaffold has an open-celled structure for promoting tissue ingrowth.

18. The product of claim 1 comprising a tissue expander.

19. The product of claim 1 comprising an implantable articulating surface for a load bearing joint.

20. The product of claim 19 wherein the articulating surface is fixed to bone with internal fixators comprising at least one of screws or sutures.

21. The product of claim 19 wherein the articulating surface is arranged and configured to be fixed to bone with a glue.

22. The product of claim 21 wherein the glue comprises a collagen glue.

23. The product of claim 1 comprising a cartilage replacement.

24. The product according to the process of claim 2.
25. The product according to the process of claim 3.
26. The product according to the process of claim 4.
27. The product according to the process of claim 5.
28. The product according to the process of claim 6.
29. The product according to the process of claim 8.
30. The product according to the process of claim 10.

* * * * *